US010710019B2

(12) United States Patent
Tanaka et al.

(10) Patent No.: US 10,710,019 B2
(45) Date of Patent: Jul. 14, 2020

(54) PRESSURE SWING ADSORPTION TYPE OF GAS PRODUCTION DEVICE

(71) Applicant: Osaka Gas Co., Ltd., Osaka-shi (JP)

(72) Inventors: Hiroshi Tanaka, Osaka (JP); Kota Yokoyama, Osaka (JP)

(73) Assignee: Osaka Gas Co., Ltd., Osaka (JP)

( * ) Notice: Subject to any disclaimer, the term of this patent is extended or adjusted under 35 U.S.C. 154(b) by 149 days.

(21) Appl. No.: 16/088,571

(22) PCT Filed: Mar. 13, 2017

(86) PCT No.: PCT/JP2017/009954
§ 371 (c)(1),
(2) Date: Sep. 26, 2018

(87) PCT Pub. No.: WO2017/169688
PCT Pub. Date: Oct. 5, 2017

(65) Prior Publication Data
US 2019/0126187 A1    May 2, 2019

(30) Foreign Application Priority Data

Mar. 31, 2016   (JP) .................................. 2016-072351

(51) Int. Cl.
*B01D 53/047* (2006.01)
*C07C 7/12* (2006.01)
(Continued)

(52) U.S. Cl.
CPC ....... *B01D 53/047* (2013.01); *B01D 53/0454* (2013.01); *B01D 53/053* (2013.01);
(Continued)

(58) Field of Classification Search
CPC .................. B01D 53/147; B01D 53/0454; B01D 53/053; B01D 53/22; B01D 53/229;
(Continued)

(56) References Cited

U.S. PATENT DOCUMENTS 4,229,188 A * 10/1980 Intille .................... B01D 53/04
95/100
4,238,204 A    12/1980 Perry
(Continued)

FOREIGN PATENT DOCUMENTS

JP     5651223 A    5/1981
JP     6391119 A    4/1988
(Continued)

*Primary Examiner* — Jason M Greene
(74) *Attorney, Agent, or Firm* — The Webb Law Firm (57) ABSTRACT

A pressure swing adsorption gas production device that enables performing a desorption process in adsorption towers is provided. The device includes an off gas discharge route connected to the adsorption towers, a membrane separation unit with a separation membrane allowing miscellaneous gas in the off gas discharge route to pass faster than purification target gas, an off gas tank, and a pressure boosting unit that raises the pressure of and supplies the off gas to the membrane separation unit. The off gas tank and the pressure boosting unit are upstream of the membrane separation unit. The device includes a recycle gas return route via which some recycle gas is returned to the source gas supply route. The operation control unit adjusts the off gas adjustment unit so the off gas discharge flow rate is a flow rate where the amount of off gas discharged from one adsorption tower during the desorption process is equivalent to the amount of off gas discharged from the off gas tank when the one adsorption tower starts the desorption process until another starts the desorption process.

8 Claims, 6 Drawing Sheets

(51) Int. Cl.
*C07C 7/144* (2006.01)
*B01D 53/053* (2006.01)
*C07C 9/04* (2006.01)
*B01D 53/04* (2006.01)
*B01D 53/22* (2006.01)
*B01D 53/30* (2006.01)

(52) U.S. Cl.
CPC ............ *B01D 53/229* (2013.01); *B01D 53/30* (2013.01); *C07C 7/12* (2013.01); *C07C 7/144* (2013.01); *C07C 9/04* (2013.01); *B01D 2253/102* (2013.01); *B01D 2253/116* (2013.01); *B01D 2256/245* (2013.01); *B01D 2257/504* (2013.01); *B01D 2258/05* (2013.01); *B01D 2259/404* (2013.01); *B01D 2259/40009* (2013.01); *B01D 2259/40016* (2013.01); *B01D 2259/40033* (2013.01); *B01D 2259/40039* (2013.01); *B01D 2259/40041* (2013.01); *B01D 2259/40069* (2013.01); *B01D 2259/40075* (2013.01)

(58) Field of Classification Search
CPC .............. B01D 53/30; B01D 2257/504; B01D 2259/40009; B01D 2259/40016; B01D 2259/40033; B01D 2259/40039; B01D 2259/40041; B01D 2259/40069; B01D 2259/40075; B01D 2259/404; C07C 7/12; C07C 7/144
See application file for complete search history.

(56) References Cited

U.S. PATENT DOCUMENTS

| | | | |
|---|---|---|---|
| 4,765,804 A | | 8/1988 | Lloyd-Williams et al. |
| 4,783,203 A | * | 11/1988 | Doshi ................. B01D 53/229 95/50 |
| 5,753,010 A | * | 5/1998 | Sircar ................. B01D 53/047 95/105 |
| 8,460,630 B2 | | 6/2013 | Niitsuma et al. |
| 2010/0129284 A1 | | 5/2010 | Niitsuma et al. |
| 2012/0241678 A1 | * | 9/2012 | Valentin ............... B01D 53/047 252/373 |
| 2018/0111831 A1 | * | 4/2018 | Adamopoulos ........ B01D 53/02 |

FOREIGN PATENT DOCUMENTS

| | | |
|---|---|---|
| JP | 6447421 A | 2/1989 |
| JP | 312212 A | 1/1991 |
| JP | 2008247632 A | 10/2008 |
| JP | 5039407 B2 | 7/2012 |
| WO | 2014104196 A1 | 7/2014 |

* cited by examiner

| STEP | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Tower A | Standby | Source pressure boost, adsorption | | Adsorption pressure equalization AB | Standby | Pressure equalization AC | Pressure equalization AD | Pressure reduction | | | Pressure equalization BA | Standby | | Pressure equalization CA | Standby | Adsorption pressure equalization DA |
| Tower B | Pressure equalization DB | | Standby | Adsorption pressure equalization AB | Source pressure boost, adsorption | | | Adsorption pressure equalization BC | Standby | Pressure equalization BD | Pressure equalization BA | | Pressure reduction | | Pressure equalization CB | Standby |
| Tower C | Pressure reduction | | Pressure equalization DC | Standby | | Pressure equalization AC | Standby | Adsorption pressure equalization BC | | Source pressure boost, adsorption | | Adsorption pressure equalization CD | Standby | Pressure equalization CA | Pressure equalization CB | Pressure reduction |
| Tower D | Standby | Pressure equalization DB | Pressure equalization DC | Adsorption pressure equalization AB | Pressure reduction | | Pressure equalization AD | Standby | | Pressure equalization BD | Standby | Adsorption pressure equalization CD | | Source pressure boost, adsorption | | Adsorption pressure equalization DA |
| Time (sec) | X | t1 | t2 | t3 | X | t1 | t2 | t3 | X | t1 | t2 | t3 | X | t1 | t2 | t3 |

Fig.4

| Process correction value calculation table | | | | | | | |
|---|---|---|---|---|---|---|---|
| Source gas methane concentration (%) | 57 | 58 | 59 | 60 | 61 | 62 | 63 |
| Process correction value (sec) | -6 | -4 | -2 | 0 | 2 | 4 | 6 |

Fig.5

| Behavior during control according to process correction value calculation table | | | | | | | |
|---|---|---|---|---|---|---|---|
| Overall adsorption process count | y | y+1 | y+2 | y+3 | y+4 | y+5 | y+6 |
| Average source gas methane concentration in cycle | 57 | 59 | 57 | 60 | 60 | 62 | – |
| X: adsorption time correction value (sec) | 100 | 94 | 98 | 94 | 100 | 100 | 104 |

(Initial value of X is 100)

| Process correction value calculation table | | | | | | | |
|---|---|---|---|---|---|---|---|
| Product gas methane concentration (%) | 82 | 83 | 84 | 85 | 86 | 87 | 88 |
| Process correction value (sec) | −3 | −2 | −1 | 0 | 1 | 2 | 3 |

Fig.14

| Behavior during control according to process correction value calculation table | | | | | | | |
|---|---|---|---|---|---|---|---|
| Overall adsorption process count | y | y+1 | y+2 | y+3 | y+4 | y+5 | y+6 |
| Average product gas methane concentration in cycle | 82 | 84 | 85 | 86 | 86 | 84 | − |
| X: adsorption time correction value (sec) | 100 | 97 | 96 | 96 | 97 | 98 | 97 |

(Initial value of X is 100)

Fig.15

| Process correction value calculation table | | | | | | | |
|---|---|---|---|---|---|---|---|
| Source gas methane concentration (%) | 57 | 58 | 59 | 60 | 61 | 62 | 63 |
| Process correction value (sec) | −6 | −4 | −2 | 0 | 2 | 4 | 6 |

Fig.16

| Process correction value calculation table | | | | | | | |
|---|---|---|---|---|---|---|---|
| Product gas methane concentration (%) | 82 | 83 | 84 | 85 | 86 | 87 | 88 |
| Process correction value (sec) | −3 | −2 | −1 | 0 | 1 | 2 | 3 |

Fig.17

| Behavior during control according to process correction value calculation table | | | | | | | |
|---|---|---|---|---|---|---|---|
| Overall adsorption process count | y | y+1 | y+2 | y+3 | y+4 | y+5 | y+6 |
| Average source gas methane concentration in cycle | 57 | 59 | 57 | 60 | 60 | 62 | − |
| Average product gas methane concentration in cycle | 82 | 84 | 85 | 86 | 86 | 84 | − |
| X: adsorption time correction value (sec) | 100 | 91 | 94 | 90 | 97 | 98 | 101 |

(Initial value of X is 100)

PRESSURE SWING ADSORPTION TYPE OF GAS PRODUCTION DEVICE

This application is the United States national phase of International Application No. PCT/JP2017/009954 filed Mar. 13, 2017, and claims priority to Japanese Patent Application No. 2016-072351 filed Mar. 31, 2016, the disclosures of which are hereby incorporated in their entirety by reference.

TECHNICAL FIELD

The present invention relates to a pressure swing adsorption type of gas production device that includes: a plurality of adsorption towers that are each filled with an adsorbent to which a miscellaneous gas is adsorbed from a source gas that includes a purification target gas and the miscellaneous gas, a source gas supply route being connected to one end side of each of the adsorption towers, a purification target gas discharge route being connected to another end side of each of the adsorption towers, and an off gas discharge route being connected to each of the adsorption towers; an operation control unit that causes the adsorption towers to successively perform, with different phases, an operation cycle that includes an adsorption process in which the miscellaneous gas is adsorbed from the source gas supplied via the source gas supply route such that the purification target gas is discharged via the purification target gas discharge route, and a desorption process in which the miscellaneous gas is discharged via the off gas discharge route; a membrane separation unit that is provided in the off gas discharge route and includes a separation membrane that allows the miscellaneous gas to pass faster than the purification target gas; and a recycle gas return route via which recycle gas that did not pass through the separation membrane is returned to the source gas supply route.

BACKGROUND ART

With such a pressure swing adsorption type of gas production device, the off gas discharged from the adsorption towers contains the purification target gas, and therefore a membrane separation unit is used to separate miscellaneous gases from the off gas, and then the off gas is returned to the source gas supply route as recycle gas, thus improving the purification target gas production efficiency while also reducing the load on the adsorption towers.

In one conventional example of such a pressure swing adsorption type of gas production device, off gas discharged from adsorption towers via an off gas discharge route is guided to a pressure boosting unit (pressure booster), and then after the pressure is boosted by the pressure boosting unit, the off gas is guided to a membrane separation unit (e.g., see Patent Document 1).

Patent Document 1 discloses that the source gas is a hydrogen-containing gas that contains hydrogen as the purification target gas, and contains carbon dioxide and methane as miscellaneous gases.

It should be noted that in the configuration in Patent Document 1, after passing through the membrane separation unit, the hydrogen-containing gas is supplied to a carbon dioxide separating membrane for separating out carbon dioxide, and the resulting hydrogen-containing gas is returned to the source gas supply route as recycle gas.

Note that although not described in detail in Patent Document 1, in order to avoid the case where the pressure boosting unit is negatively affected by operating in an empty operation state where no off gas is present, and in order to reduce the internal pressure in the off gas discharge route in the desorption process, it can be thought that the output rate of the pressure boosting unit is defined such that the amount of off gas discharged from an adsorption tower in each desorption process is equivalent to the amount of output from the pressure boosting unit in the period from when one adsorption tower starts the desorption process until when another adsorption tower starts the desorption process.

PRIOR ART DOCUMENTS

Patent Documents

Patent Document 1: JP 5039407B

DISCLOSURE OF THE INVENTION

Problem to be Solved by the Invention

In conventional pressure swing adsorption type of gas production devices, the off gas discharged from the adsorption towers via the off gas discharge route is boosted in pressure by the pressure boosting unit while filling the off gas discharge route, and is then guided to the membrane separation unit, and therefore it is difficult to sufficiently lower the internal pressure in the adsorption towers in the desorption process, and thus there is a risk of thus difficulty in favorably performing the desorption process.

More specifically, although the off gas discharged from the adsorption towers is successively fed to the membrane separation unit by the pressure boosting unit, there is a tendency for the off gas discharge route to continuously be filled with high-pressure off gas, and therefore it is difficult to sufficiently lower the internal pressure in the off gas discharge route, thus consequently making it difficult to sufficiently lower the internal pressure in the adsorption towers in the desorption process, and therefore there is a risk of difficulty in favorably performing the desorption process.

The present invention was achieved in light of the situation described above, and an object of the present invention is to provide a pressure swing adsorption type of gas production device that enables favorably performing the desorption process in adsorption towers.

Means for Solving Problem

A pressure swing adsorption type of gas production device according to the present invention includes:

a plurality of adsorption towers that are each filled with an adsorbent to which a miscellaneous gas is adsorbed from a source gas that includes a purification target gas and the miscellaneous gas, a source gas supply route being connected to one end side of each of the adsorption towers, a purification target gas discharge route being connected to another end side of each of the adsorption towers, and an off gas discharge route being connected to each of the adsorption towers;

an operation control unit that causes the adsorption towers to successively perform, with different phases, an operation cycle that includes an adsorption process in which the miscellaneous gas is adsorbed from the source gas supplied via the source gas supply route such that the purification target gas is discharged via the purification target gas discharge route, and a desorption process in which the miscellaneous gas is discharged via the off gas discharge route;

a membrane separation unit that is provided in the off gas discharge route and includes a separation membrane that allows the miscellaneous gas to pass faster than the purification target gas; and a recycle gas return route via which recycle gas that did not pass through the separation membrane is returned to the source gas supply route, and has a characteristic configuration in which a pressure boosting unit and an off gas tank are provided on an upstream side of the membrane separation unit in the off gas discharge route, the off gas tank storing off gas that is discharged via the off gas discharge route in the desorption process, and the pressure boosting unit raising a pressure of the off gas stored in the off gas tank and supplying the off gas to the membrane separation unit for membrane separation in the membrane separation unit, the pressure swing adsorption type of gas production device further comprises an off gas adjustment unit that adjusts a discharge flow rate of the off gas that is discharged from the off gas tank, and the operation control unit adjusts the off gas adjustment unit such that the discharge flow rate of the off gas is a flow rate according to which the amount of off gas discharged from one of the adsorption towers each time the desorption process is performed is equivalent to the amount of off gas discharged from the off gas tank in a period from when the one adsorption tower starts the desorption process until when another adsorption tower starts the desorption process.

In other words, the off gas discharged from an adsorption tower in the desorption process is temporarily stored in the off gas tank, the stored off gas is boosted in pressure by the pressure boosting unit and supplied to the membrane separation unit, the miscellaneous gas is separated out by the membrane separation unit, and the resulting off gas is returned as recycle gas to the source gas supply route via the recycle gas return route.

Also, due to the operation control unit adjusting the off gas adjustment unit, the discharge flow rate of the off gas discharged from the off gas tank is maintained at a flow rate according to which the amount of off gas discharged from one adsorption tower each time the desorption process is performed is equivalent to the amount of off gas discharged from the off gas tank in the period from when the one adsorption tower starts the desorption process until when another adsorption tower starts the desorption process, thus suppressing the case where the internal pressure of the off gas tank becomes excessively high or excessively low.

Accordingly, because the off gas discharged from an adsorption tower in the desorption process is temporarily stored in the off gas tank, the desorption process can be favorably performed by setting the internal pressure of the off gas tank to a low pressure that is suited to performing the desorption process.

In other words, the off gas is temporarily stored in the off gas tank, and the stored off gas is boosted in pressure by the pressure boosting unit and supplied to the membrane separation unit, thus making it possible for the off gas to be stored in the off gas tank at a sufficiently low pressure, and this makes it possible to favorably perform the desorption process.

Moreover, by adjusting the off gas discharge flow rate, it is possible to suppress the case where the internal pressure of the off gas tank becomes excessively high or excessively low, and therefore it is possible to favorably perform the desorption process while also avoiding the case where the desorption process cannot performed appropriately due to the internal pressure of the off gas tank being excessively high, and the case where the pressure boosting unit is negatively influenced due to the internal pressure of the off gas tank being excessively low.

In other words, according to the above characteristic configuration of the pressure swing adsorption type of gas production device of the present invention, the desorption process can be favorably performed in the adsorption towers.

In another characteristic configuration of the pressure swing adsorption type of gas production device of the present invention, the device further includes a pressure sensor that detects an internal pressure in the off gas tank, and the operation control unit adjusts, based on detection information from the pressure sensor, the off gas adjustment unit such that the discharge flow rate of the off gas is a flow rate according to which a local minimum value of the internal pressure of the off gas tank, which repeatedly increases and decreases, is maintained at a set pressure.

In other words, based on detection information from the pressure sensor that detects the internal pressure of the off gas tank, the operation control unit adjusts the off gas discharge flow rate to a flow rate according to which the local minimum value of the internal pressure of the off gas tank, which repeatedly increases and decreases, is maintained at a set pressure, and as a result, the off gas discharge flow rate is adjusted to a flow rate according to which the amount of off gas discharged from one adsorption tower each time the desorption process is performed is equivalent to the amount of off gas discharged from the off gas tank in the period from when the one adsorption tower starts the desorption process until when another adsorption tower starts the desorption process.

In this way, the off gas discharge flow rate is adjusted based on detection information from the pressure sensor that detects the internal pressure of the off gas tank, thus making it possible to simplify the configuration for adjusting the off gas discharge flow rate and also reduce the cost.

In other words, according to another characteristic configuration of the pressure swing adsorption type of gas production device of the present invention, it is possible to simplify the configuration for adjusting the off gas discharge flow rate and also reduce the cost.

In another characteristic configuration of the pressure swing adsorption type of gas production device of the present invention, the operation control unit changes/adjusts an adsorption time for which the adsorption process is performed, based on at least one of a concentration of the purification target gas in the source gas and a concentration of the purification target gas discharged from the adsorption tower, and in a case of changing the adsorption time, the operation control unit adjusts the off gas adjustment unit so as to correct the discharge flow rate of the off gas discharged from the off gas tank to a flow rate according to which the amount of off gas discharged from one of the adsorption towers before the change in the adsorption time is equivalent to the amount of off gas discharged from the off gas tank in a period from when the one adsorption tower starts the desorption process after the change in the adsorption time until when another adsorption tower starts the desorption process.

In other words, the operation control unit changes the adsorption time for which the adsorption process is performed, based on at least one of the concentration of the purification target gas in the source gas and the concentration of the purification target gas discharged from the adsorption tower, and therefore even if the concentration of the purification target gas in the source gas changes for example, the concentration of the purification target gas discharged via the purification target gas discharge route can be maintained at an appropriate concentration.

In other words, for example, the adsorption time is set shorter the lower the concentration of the purification target gas in the source gas is, and similarly, the adsorption time is set shorter the lower the concentration of the purification target gas discharged from the adsorption towers is, and therefore the concentration of the purification target gas discharged from the adsorption towers can be maintained at an appropriate concentration.

It should be noted that a configuration is possible in which, based on the concentration of the purification target gas in the source gas and the concentration of the purification target gas discharged from the adsorption towers, the adsorption time is set in a feed-forward manner so as to be shorter the lower the concentration of the purification target gas in the source gas is, and the adsorption time is corrected in a feed-back manner so as to be shorter the lower the concentration of the purification target gas discharged from the adsorption towers is.

Also, in the case of changing the adsorption time, the operation control unit adjusts the off gas adjustment unit so as to correct the discharge flow rate of the off gas discharged from the off gas tank to a flow rate according to which the amount of off gas discharged from one of the adsorption towers before the change in the adsorption time is equivalent to the amount of off gas discharged from the off gas tank in a period from when the one adsorption tower starts the desorption process after the change in the adsorption time until when another adsorption tower starts the desorption process.

Accordingly, even if the adsorption time is changed, it is possible to suppress the case where the internal pressure of the off gas tank becomes excessively high or excessively low, and to avoid negatively influencing the adsorption process and negatively influencing the pressure boosting unit.

More specifically, when the adsorption time is changed/adjusted, an immediate change occurs in the time for which the off gas discharged from one of the adsorption towers can be discharged from the off gas tank.

Accordingly, immediately after the adsorption time is changed/adjusted, off gas is discharged from the adsorption tower that performed the adsorption process before the adsorption time was changed/adjusted, and therefore the amount of off gas discharged from the adsorption tower does not change immediately after the adsorption time is changed/adjusted.

As a result, when the adsorption time for performing the adsorption process is changed/adjusted to a shorter time, the off gas discharge flow rate becomes insufficient, and when the adsorption time for performing the adsorption process is changed/adjusted to a longer time, the off gas discharge flow rate becomes excessive, and thus the internal pressure of the off gas tank becomes excessively high or low.

According to the above characteristic configuration, in the case where the adsorption time is changed, the discharge flow rate of the off gas tank is corrected to a flow rate according to which the amount of off gas discharged from one of the adsorption towers before the change in the adsorption time is equivalent to the amount of off gas discharged from the off gas tank in a period from when the one adsorption tower starts the desorption process after the change in the adsorption time until when another adsorption tower starts the desorption process, thus making it possible to suppress a large increase or decrease in the internal pressure of the off gas tank.

In other words, according to another characteristic configuration of the pressure swing adsorption type of gas production device of the present invention, by changing/adjusting the adsorption time, the concentration of the purification target gas discharged from the adsorption tower can be maintained at an appropriate concentration, and moreover, in the case where the adsorption time is changed, it is possible to avoid negatively influencing the adsorption process and negatively influencing the pressure boosting unit.

In another characteristic configuration of the pressure swing adsorption type of gas production device of the present invention, the device further includes a source gas adjustment unit that adjusts a source gas supply rate of source gas supplied to the adsorption tower via the source gas supply route, and the operation control unit adjusts the source gas adjustment unit so as to correct the source gas supply rate to a lower value in a case where the discharge flow rate of the off gas tank is corrected to a higher value, and to correct the source gas supply rate to a higher value in a case where the discharge flow rate is corrected to a lower value.

In other words, in the case of correcting the off gas discharge flow rate to a higher value, the operation control unit corrects the source gas supply rate to a lower value, and therefore even if the off gas discharge flow rate is corrected to a higher value, the concentration of the purification target gas discharged from the adsorption towers can be maintained at an appropriate concentration, and even if the off gas discharge flow rate is corrected to a lower value, the operation control unit corrects the source gas supply rate to a higher value, thus making it possible to suppress a decrease in the efficiency of production of the purification target gas.

More specifically, if the off gas discharge flow rate is increased, then the recycle gas amount increases, and the amount of gas supplied to an adsorption tower increases rapidly, and therefore the amount of miscellaneous gas that is not adsorbed to the adsorption tower tends to increase, and the concentration of the purification target gas discharged from the adsorption tower decreases. However, by correcting the source gas supply rate to a lower value if the off gas discharge flow rate is corrected to a higher value, it is possible to avoid a rapid increase in the amount of gas supplied to the adsorption tower, and to maintain an appropriate concentration for the purification target gas discharged from the adsorption tower.

Also, if the off gas discharge flow rate is corrected to a lower value, the source gas supply rate is corrected to a higher value, thus suppressing a decrease in the amount of purification target gas that is refined.

It should be noted that, in the case where the adsorption time for performing the adsorption process is changed based on the concentration of the purification target gas discharged from an adsorption tower, if the concentration of the purification target gas discharged from the adsorption tower falls below an appropriate concentration, the adsorption time is again accordingly corrected to a shorter time, and there is a risk of inviting an abnormal situation in which the off gas discharge flow rate is repeatedly increased, but by correcting the source gas supply rate to a lower value if the off gas discharge flow rate is corrected to a higher value, it is possible to suppress the case of inviting such an abnormal situation.

In other words, according to the above other characteristic configuration of the pressure swing adsorption type of gas production device of the present invention, the concentration of the purification target gas discharged from the adsorption tower can be maintained at an appropriate concentration even in the case where the off gas discharge flow rate is corrected to a higher rate.

In another characteristic configuration of the pressure swing adsorption type of gas production device of the present invention, the source gas is a methane-containing gas that contains 40% or more methane as the purification target gas, and the purification target gas discharged via the purification target gas discharge route is a product gas that contains 80% or more methane.

In other words, by providing the adsorption tower and the membrane separation unit, a methane-containing gas that contains 40% or more methane as a purification target gas can be efficiently refined to a product gas that contains 80% or more methane.

It should be noted that biogas is one example of a methane-containing gas. This biogas contains approximately 40 to 60% methane and 60 to 40% carbon dioxide, and even this biogas can be efficiently refined to a product gas that contains 80% or more methane.

In other words, according to the above other characteristic configuration of the present invention, a methane-containing gas that contains 40% or more methane as the purification target gas can be efficiently refined to a product gas that contains 80% or more methane.

EMBODIMENT

First Embodiment

The following describes an embodiment of the present invention with reference to the drawings.

Overall Configuration of Pressure Swing Adsorption Type of Gas Production Device In the configuration of the present embodiment, a source gas G is a biogas that contains 40% or more methane as a purification target gas and contains carbon dioxide or the like as a miscellaneous gas, the miscellaneous gas is adsorbed to an adsorbent in adsorption towers 1, and methane gas containing 80% or more methane is discharged as a product gas H from the adsorption towers 1.

Specifically, the biogas serving as the source gas G contains methane and carbon dioxide as main components, and has a methane content percentage of approximately 60%, for example. Also, the pressure swing adsorption type of gas production device of the present embodiment is configured to perform gas refinement for obtaining the product gas H that contains 80% or more methane.

It should be noted that the adsorbent that fills the adsorption towers 1 can be a material that has, as a main component, at least one type of material selected from activated carbon, molecular sieve carbon, zeolite, and a porous metal complex. The present embodiment uses, for example, molecular sieve carbon in which the pore volume does not exceed 0.01 cm$^3$/g at a pore diameter of 0.38 nm or more, as measured by the MP method, and the pore volume is 0.20 cm$^3$/g or more at the pore diameter of 0.34 nm.

Figure 1:
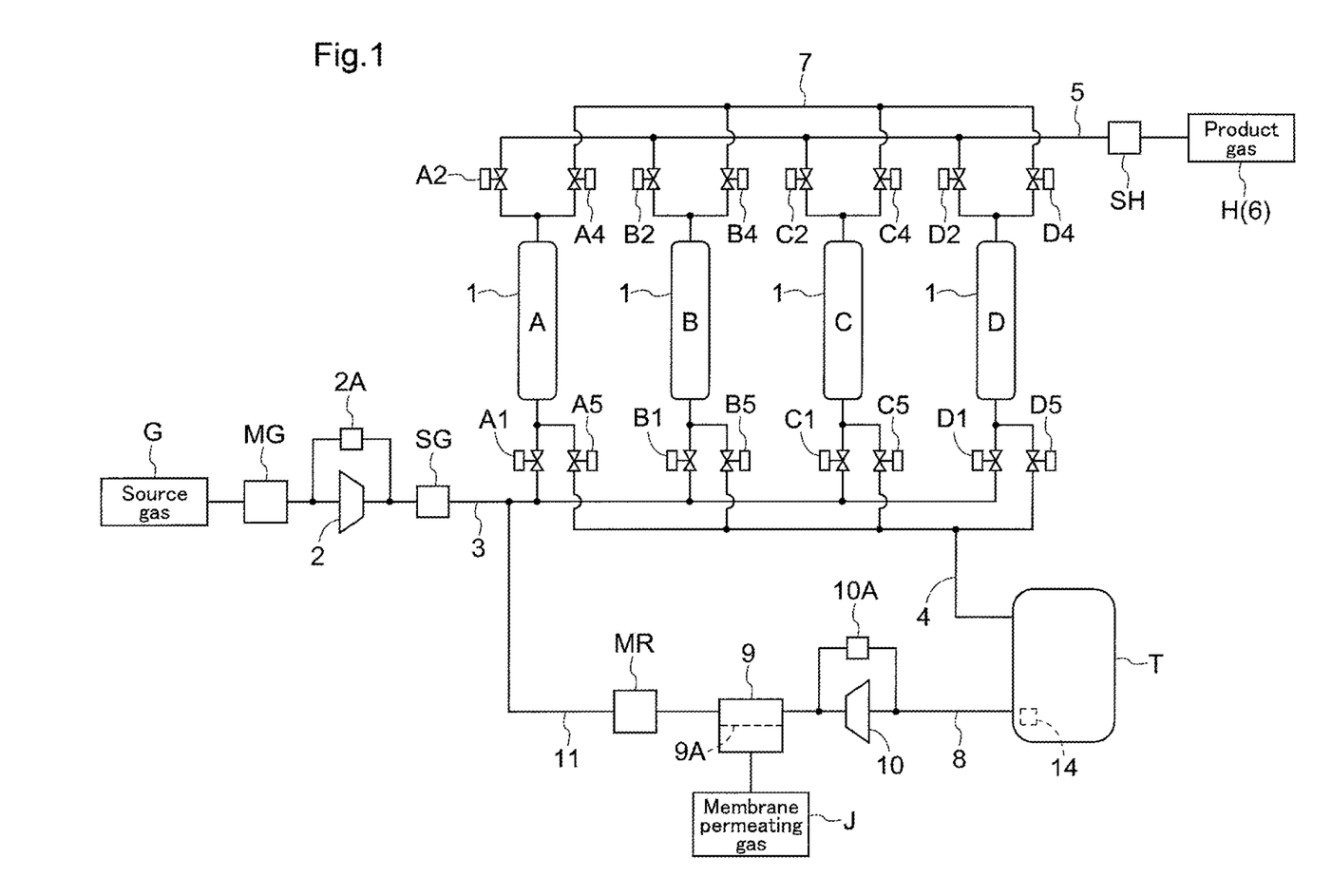
FIG. 1 is a schematic diagram showing a pressure swing adsorption type of gas production device.

As shown in FIG. 1, a tower A, a tower B, a tower C, and a tower D are provided as four adsorption towers 1, and the lower end sides of the four adsorption towers 1 are connected to a source gas supply route 3 for supplying the source gas G at a pressure boosted by a compressor 2 that serves as a source pressure boosting unit, and are also connected to an off gas discharge route 4 for discharging off gas.

The compressor 2 is provided with a back pressure valve 2A for maintaining the supply pressure at a set value (e.g., 750 kPaG).

A source gas adjustment unit MG for adjusting the source gas supply rate to a target supply rate is provided on the upstream side of the compressor 2 in the source gas supply route 3.

The source gas adjustment unit MG is constituted using a massflow controller, and is configured to detect the flow rate of the source gas G in the source gas supply route 3, and control the flow rate of the source gas G such that the detected flow rate becomes a target flow rate that is indicated by an instruction given by a later-described operation control unit F (see FIG. 2). Note that details of this massflow controller are widely known, and therefore a detailed description will not be given in the present embodiment.

Also, the four adsorption towers 1 are respectively provided with source gas supply valves A1, B1, C1, and D1 for opening and closing the source gas supply route 3, and off gas discharge valves A5, B5, C5, and D5 for opening and closing the off gas discharge route 4.

Also, a source-side concentration sensor SG for detecting the methane gas concentration of the purification target gas in the source gas G (source gas methane concentration) is provided on the downstream side of the compressor 2 in the source gas supply route 3.

A product gas feed route 5 is provided on the upper end sides of the four adsorption towers 1 as a purification target gas discharge route for discharging the product gas H, and the product gas H passes through this product gas feed route 5 and is stored in a product gas tank 6. Also, upper portions of the four adsorption towers 1 are connected to a tower connection route 7 for connecting the four adsorption towers 1 to each other.

Also, the four adsorption towers 1 are respectively provided with product gas discharge valves A2, B2, C2, and D2 for opening and closing the product gas feed route 5, and communication on/off valves A4, B4, C4, and D4 for opening and closing the tower connection route 7.

It should be noted that a product-side concentration sensor SH for detecting the methane gas concentration of the purification target gas in the product gas H (product gas methane concentration) is provided in the product gas feed route 5.

An off gas tank T for storing off gas is connected to the off gas discharge route 4, an off gas feed route 8 for feeding the stored off gas is connected to the off gas tank T, and the off gas feed route 8 is provided with a membrane separation unit 9 that includes a separation membrane 9A, and a booster pump 10 that serves as a pressure boosting unit for raising the pressure of the off gas and then supplying it to the membrane separation unit 9.

The booster pump 10 is provided with a pump back pressure valve 10A for maintaining the supply pressure at a set target value (e.g., 780 kPaG).

The separation membrane 9A of the membrane separation unit 9 is made of a material that allows the miscellaneous gas, which contains carbon dioxide as a main component, to pass faster than methane, which is the purification target gas. Specifically, by using a material that allows the miscellaneous gas to pass faster than methane, almost no methane, which is the purification target gas, passes through, or substantially no methane passes through, and only the miscellaneous gas, which contains carbon dioxide as a main component, in the off gas stored in the off gas tank T is separated out as membrane permeating gas J.

This separation membrane 9A is made of, as a main component, at least one material selected from among cellulose acetate, polyamide, polyimide, polysulfone, polytetrafluoroethylene, polyethersulfone, a carbon film, a microporous glass composite film, DDR-type zeolite, multi-branched polyimide silica, and polydimethylsiloxane.

A recycle gas return route 11 is provided, by which the off gas (containing methane as a main component) that did not pass through the separation membrane 9A of the membrane separation unit 9 is supplied to the source gas supply route 3 as recycle gas.

Also, an off gas adjustment unit MR, which adjusts the discharge flow rate of the off gas discharged from the off gas tank T, is provided in the recycle gas return route 11 in order to maintain the flow rate of the recycle gas at a target flow rate.

Similarly to the source gas adjustment unit MG, the off gas adjustment unit MR is constituted using a massflow controller, and is configured to detect the flow rate of the recycle gas in the recycle gas return route 11, and control the flow rate of the recycle gas such that the detected flow rate becomes a target flow rate that is indicated by an instruction given by the later-described operation control unit F (see FIG. 2).

Specifically, the operation control unit F is configured to give an instruction indicating a target flow rate based on detection information from a pressure sensor 14 that detects the internal pressure in the off gas tank T (hereinafter, referred to as the off gas tank pressure), and this will be described in detail later.

It should be noted that the discharge flow rate of the off gas discharged from the off gas tank T can be adjusted by adjusting the flow rate of the recycle gas, and more specifically, the membrane permeating gas rate of the membrane separation unit 9 increases directly proportionally to an increase in the discharge flow rate of the off gas, and therefore the off gas discharge flow rate and the recycle gas flow rate are in a directly proportional relationship.

Operation Control with Pressure Swing Adsorption Type of Gas Production Device

Figure 2:
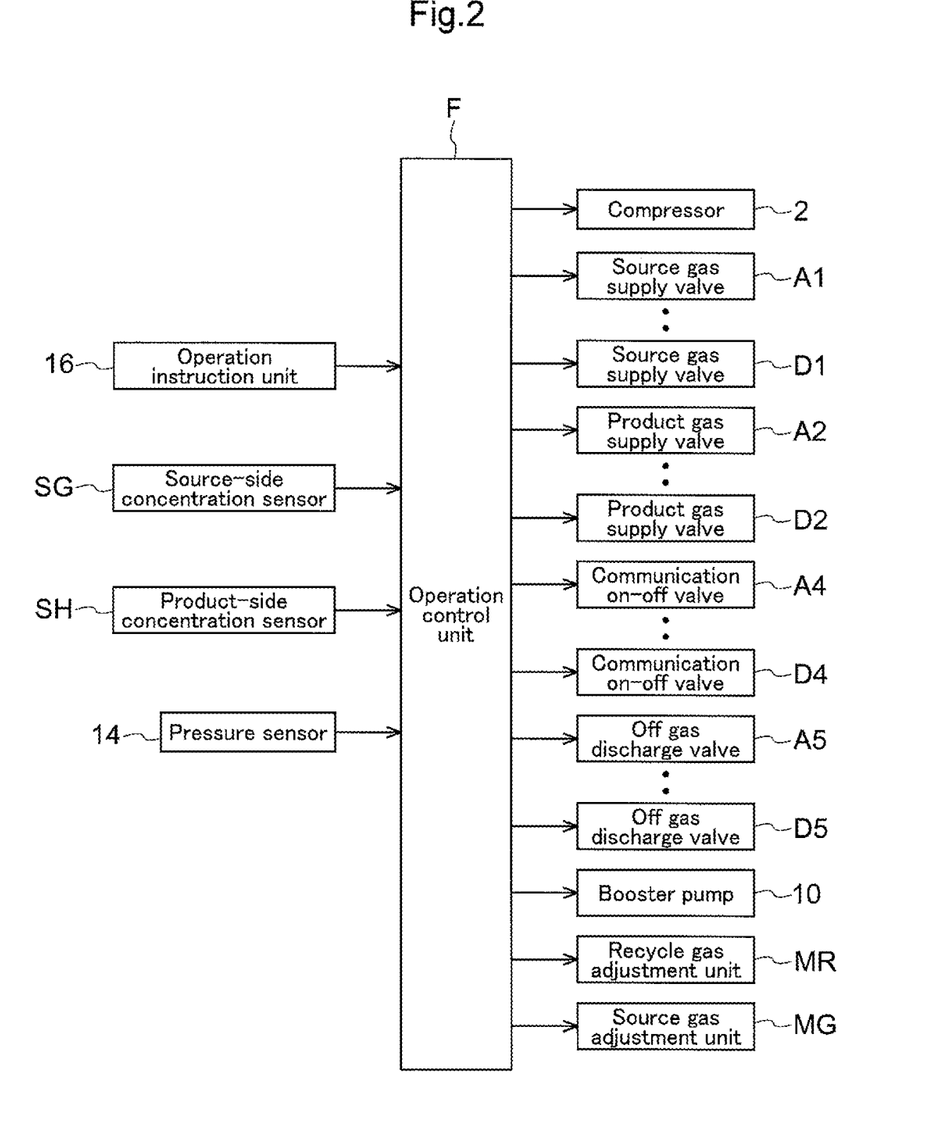
FIG. 2 is a block diagram showing a control configuration.
Figure 3:
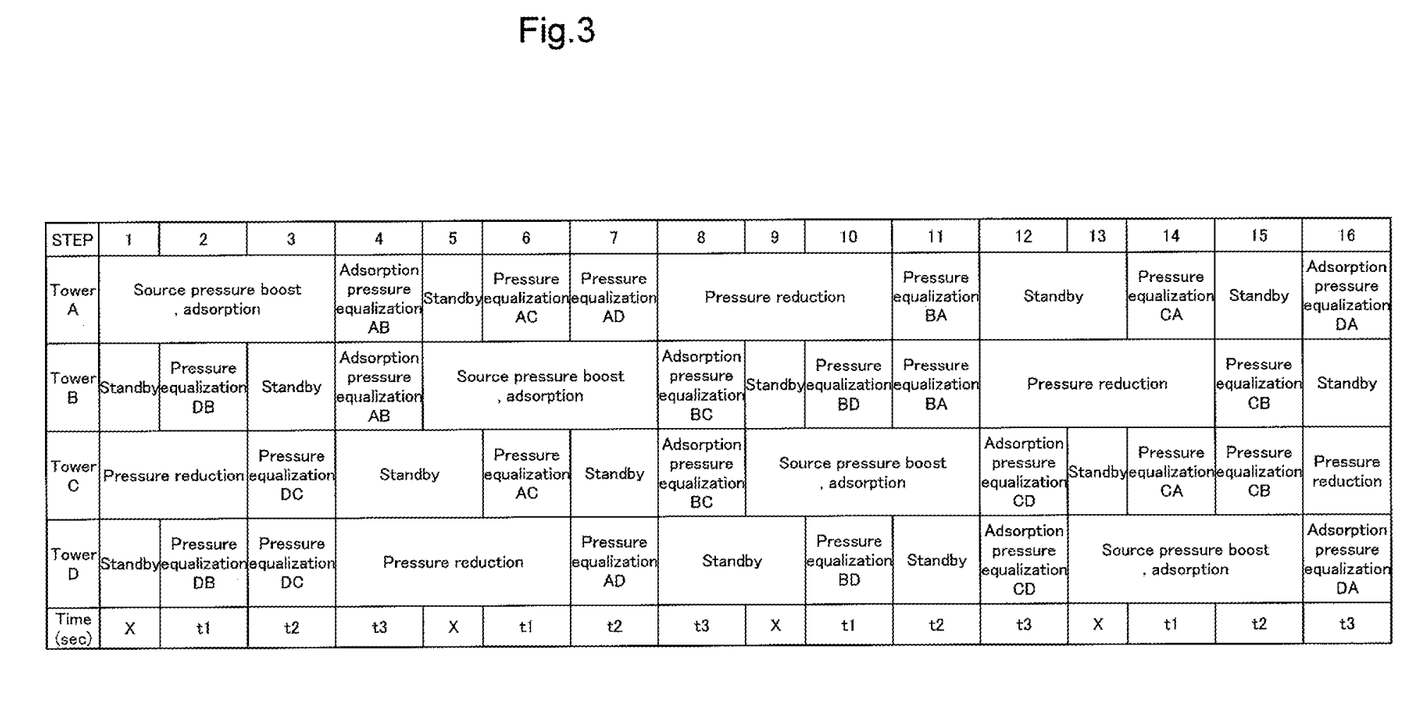
FIG. 3 is a table showing an operation cycle.

As shown in FIG. 2, an operation control unit F for controlling operation of the pressure swing adsorption type of gas production device is provided, and the operation control unit F controls the source gas supply valves A1 to D1, the product gas discharge valves A2 to D2, the communication on/off valves A4 to D4, and the off gas discharge valves A5 to D5 such that the four adsorption towers 1 perform the operation cycle shown in the table of FIG. 3.

Specifically, the operation cycle is divided into 16 steps, and the four adsorption towers 1 successively execute the operation processes with different phases.

The following describes the operation cycle of the four adsorption towers 1 by way of example of the tower A.

In steps 1 to 3, the source gas supply valve A1 and the product gas discharge valve A2 corresponding to the tower A are opened to perform source pressure boosting and adsorption that correspond to an adsorption process. Specifically, while the internal pressure of the tower A is raised, miscellaneous gases become adsorbed to the adsorbent, and the product gas H is discharged through the product gas feed route 5. It should be noted that in this adsorption process, the communication on/off valve A4 and the off gas discharge valve A5 are closed.

In step 4, the communication on/off valves A4 and B4 of the tower A and the tower B are opened to perform adsorption pressure equalization AB that corresponds to a pressure-reducing initial pressure equalization process for supplying the gas inside the tower A to the tower B. It should be noted that in this pressure-reducing initial pressure equalization process, the source gas supply valve A1, the product gas discharge valve A2, and the off gas discharge valve A5 are closed.

Note that "AB" in the term adsorption pressure equalization AB means that the gas inside the previously-described high-pressure tower A is supplied to the later-described low-pressure tower B, and the same follows for the other terms used below.

In step 5, all of the valves related to the tower A are closed, and a standby state is entered.

In step 6, the communication on/off valves A4 and C4 of the tower A and the tower C are opened to perform pressure equalization AC that corresponds to a pressure-reducing intermediate pressure equalization process for supplying the gas inside the tower A to the tower C. It should be noted that in this pressure-reducing intermediate pressure equalization process, the source gas supply valve A1, the product gas discharge valve A2, and the off gas discharge valve A5 are closed.

In step 7, the communication on/off valves A4 and D4 of the tower A and the tower D are opened to perform pressure equalization AD that corresponds to a pressure-reducing final pressure equalization process for supplying the gas inside the tower A to the tower D. It should be noted that in this pressure-reducing final pressure equalization process, the source gas supply valve A1, the product gas discharge valve A2, and the off gas discharge valve A5 are closed.

In steps 8 to 10, the off gas discharge valve A5 of the tower A is opened to perform pressure reduction that corresponds to a desorption process. It should be noted that in this desorption process, the source gas supply valve A1, the product gas discharge valve A2, and the communication on/off valve A4 are closed.

In step 11, the communication on/off valves A4 and B4 of the tower A and the tower B are opened to perform pressure equalization BA that corresponds to a pressure-boosting initial pressure equalization process for supplying the gas inside the tower B to the tower A. It should be noted that in this pressure-boosting initial pressure equalization process, the source gas supply valve A1, the product gas discharge valve A2, and the off gas discharge valve A5 are closed.

In steps 12 and 13, all of the valves related to the tower A are closed, and a standby state is entered.

In step 14, the communication on/off valves A4 and C4 of the tower A and the tower C are opened to perform pressure equalization CA that corresponds to a pressure-boosting intermediate pressure equalization process for supplying the gas inside the tower C to the tower A. In this pressure-boosting intermediate pressure equalization process, the source gas supply valve A1, the product gas discharge valve A2, and the off gas discharge valve A5 are closed.

In step 15, all of the valves related to the tower A are closed, and a standby state is entered.

In step 16, the communication on/off valves A4 and D4 of the tower A and the tower D are opened to perform adsorption pressure equalization DA that corresponds to a pressure-boosting final pressure equalization process for supplying the gas inside the tower D to the tower A. It should be noted that in this pressure-boosting final pressure equalization process, the source gas supply valve A1, the product gas discharge valve A2, and the off gas discharge valve A5 are closed.

Specifically, the operation control unit F is configured to cause the four adsorption towers 1 to successively execute, with different phases, the operation cycle that includes the adsorption process, the pressure-reducing initial pressure equalization process, the pressure-reducing intermediate pressure equalization process, the pressure-reducing final pressure equalization process, the desorption process, the pressure-boosting initial pressure equalization process, the pressure-boosting intermediate pressure equalization process, and the pressure-boosting final pressure equalization process.

In other words, the operation control unit F is configured to cause the four adsorption towers 1 to successively execute, with different phases, the operation cycle that includes the adsorption process, the pressure-reducing pressure equalization process, the desorption process, and the pressure-boosting pressure equalization process.

Also, as shown in the lower level in FIG. 3, X, t1, t2, and t3 are defined as step times [sec] for which the steps 1 to 16 are executed, and the processes are executed in accordance with the determined step times.

It should be noted that the step times in steps 1, 5, 9, and 13 are times that correspond to an adsorption time correction value X for changing/adjusting the time for which adsorption is executed in the adsorption process, and as will be described later, the time for which adsorption is executed in the adsorption process is changed/adjusted by correcting the adsorption time correction value X.

As described above, the source gas adjustment unit MG for adjusting the source gas supply rate is provided at a location on the upstream side of the compressor 2 in the source gas supply route 3, and this source gas adjustment unit MG is configured to detect the flow rate of the source gas G flowing in the source gas supply route 3 and control the source gas supply rate such that the detected flow rate becomes the target flow rate set by the operation control unit F.

Specifically, the operation control unit F receives an instruction indicating a target supply rate for the source gas G from an operation instruction unit 16, and the operation control unit F is configured to give an instruction indicating the target flow rate to the source gas adjustment unit MG based on the instructed target supply rate.

Note that target supply rates for the source gas G are empirically obtained in accordance with various types of source gas G, such as various concentrations of methane in the source gas G.

It should be noted that when operation of the pressure swing adsorption type of gas production device is started, an operator uses the operation instruction unit 16 to give the operation control unit F an instruction indicating a target flow rate for recycle gas flowing in the recycle gas return route 11, and the operation control unit F gives the off gas adjustment unit MR an instruction indicating the target flow rate, and then when an automatic operation instruction is received from the operation instruction unit 16, the operation control unit F gives an instruction indicating a target flow rate to the off gas adjustment unit MR. This will be described in detail later.

Control for Adjusting Adsorption Time

The operation control unit F is configured to change/adjust the adsorption time for which the adsorption process is performed based on detection information from the source-side concentration sensor SG.

In the configuration of the present embodiment, the adsorption time correction values X that correspond to the time for step 1, the time for step 5, the time for step 9, and the time for step 13 are all adjusted to higher or lower values at the same time.

It should be noted that the time for step 1 corresponds to the adsorption time of the tower A, the time for step 5 corresponds to the adsorption time of the tower B, the time for step 9 corresponds to the adsorption time of the tower C, and the time for step 13 corresponds to the adsorption time of the tower D.

For example, the adsorption time of the tower A is the time obtained by adding the adsorption time correction value X of step 1, the step time of step 2, and the step time of step 3, and the adsorption time of the tower A is changed/adjusted by correcting the adsorption time correction value X of step 1. The same follows for the adsorption time of the tower B, the adsorption time of the tower C, and the adsorption time of the tower D.

Figure 4:
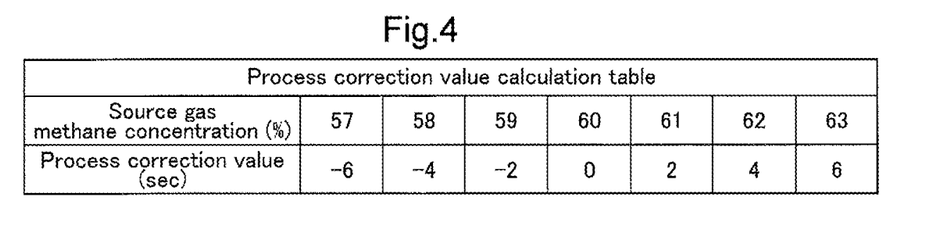
FIG. 4 is a table showing a relationship between a methane concentration in a source gas and a process correction value.

In the present embodiment, the relationship between the process correction value and the concentration of methane gas in the source gas detected by the source-side concentration sensor SG is determined in advance as shown in the table in FIG. 4.

When the pressure swing adsorption type of gas production device starts to operate, operation starts with a pre-set initial value (e.g., 100 seconds) as the adsorption time correction value X, and thereafter, each time the adsorption process is performed by the adsorption towers 1, the average value of the concentration of methane in the source gas in the corresponding cycle is obtained as the average source gas methane concentration. Note that the average source gas methane concentration is obtained by sampling the detection information from the source-side concentration sensor SG at a set time interval (e.g., 500 ms) and obtaining the average value of the sampled detection values.

Figure 5:
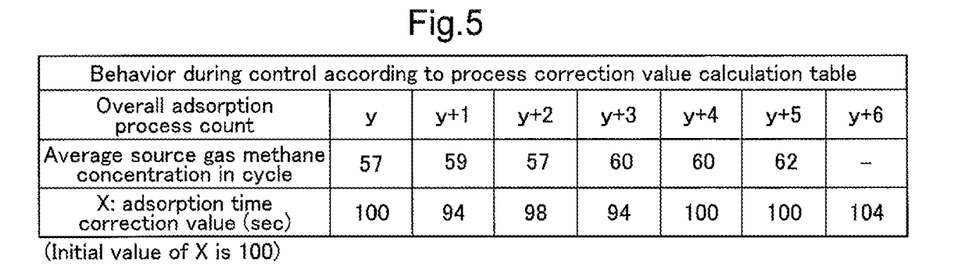
FIG. 5 is a table showing the behavior of an adsorption time correction value.

Next, as shown in FIG. 5, a process correction value is obtained based on the average source gas methane concentration and the relationship shown in FIG. 4, and the obtained process correction value is added to the current adsorption time correction value (initial value) X to obtain a new adsorption time correction value X for the next adsorption process.

For example, when the adsorption process corresponding to the overall adsorption process count y is executed with the adsorption time correction value X of 100 [sec], if the average source gas methane concentration in the current cycle is 57[%], then in the next adsorption process corresponding to the overall adsorption process count y+1, "100 [sec]" and the process correction value "−6 [sec]" are added to obtain the adsorption time correction value X of "94 [sec]", and thereafter the same follows for the subsequent adsorption processes corresponding to overall adsorption process counts y+2 to y+6.

Control of Recycle Gas Flow Rate

The operation control unit F is configured to control the off gas adjustment unit MR such that the recycle gas flow rate is a flow rate according to which the amount of off gas discharged from an adsorption tower 1 each time the desorption process is performed is equivalent to the amount of off gas discharged from the off gas tank T in the period from when one adsorption tower 1 starts the desorption process until when another adsorption tower 1 starts the desorption process.

It should be noted that the reason why the discharge flow rate of the off gas discharged from the off gas tank T can be adjusted by adjusting the flow rate of the recycle gas is that, as described above, the membrane permeating gas rate of the membrane separation unit 9 increases directly proportionally to an increase in the discharge flow rate of the off gas, and therefore the off gas discharge flow rate and the recycle gas flow rate are in a directly proportional relationship.

Specifically, the off gas discharged when one adsorption tower 1 performs the desorption process is stored in the off gas tank T, and that stored off gas needs to be discharged from the off gas tank T in the period from when one adsorption tower 1 starts the desorption process until when another adsorption tower 1 starts the next desorption process.

In the configuration of the present embodiment, Expression 1 below shows a relationship between the amount of off gas discharged from an adsorption tower 1 each time the desorption process is performed, the amount of membrane permeating gas that is separated out by the membrane separation unit 9 in the period from when one adsorption tower 1 starts the desorption process until when another adsorption tower 1 starts the desorption process, and the amount of recycle gas that is returned to the source gas supply route 3 via the recycle gas return route 11 in the period from when the one adsorption tower 1 starts the desorption process until when the other adsorption towers 1 starts the desorption process. The operation control unit F adjusts the off gas adjustment unit MR such that this relationship is maintained.

$$\text{recycle gas amount} = \text{off gas amount} - \text{membrane permeating gas amount} \qquad (1)$$

Figure 6:
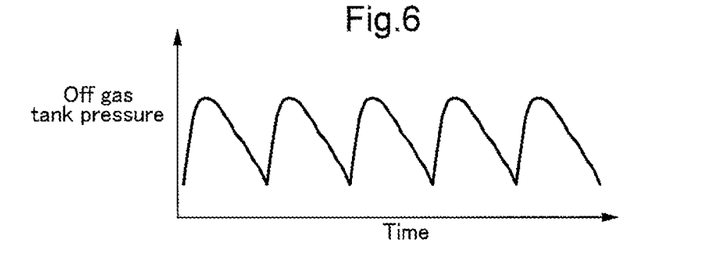
FIG. 6 is a diagram showing change in an off gas tank pressure.
Figure 7:
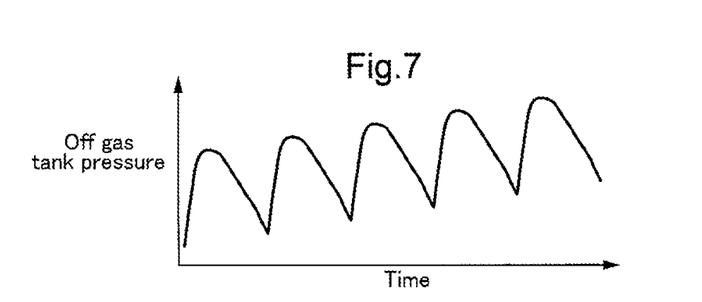
FIG. 7 is a diagram showing change in the off gas tank pressure when an off gas flow rate is excessively low.
Figure 8:
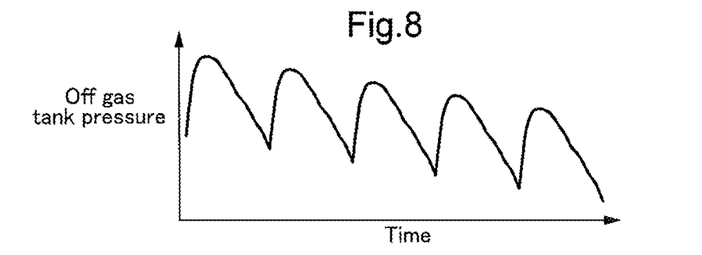
FIG. 8 is a diagram showing change in the off gas tank pressure when the off gas flow rate is excessively high.

More specifically, as shown in FIGS. 6 to 8, the off gas tank pressure, which is the internal pressure in the off gas tank T, increases as each of the four adsorption towers 1 performs the desorption process, but decreases as off gas is discharged via the off gas feed route 8.

If the relationship indicated by Expression 1 above is maintained, as shown in FIG. 6, the off gas tank pressure repeatedly increases and decreases while maintaining an appropriate minimum pressure (local minimum value) and an appropriate maximum pressure.

In contrast, if the amount of recycle gas falls below [off gas amount−membrane permeating gas amount], as shown in FIG. 7, the off gas tank pressure gradually increases, and the pressure reduction step cannot be performed appropriately.

Also, if the amount of recycle gas rises above [off gas amount−membrane permeating gas amount], as shown in FIG. 8, the off gas tank pressure gradually decreases, the off gas tank pressure of the off gas tank T becomes excessively low (negative pressure), and there is a risk of a problem occurring such as the booster pump 10 becoming damaged.

In the configuration of the present embodiment, the relationship indicated by Expression 1 above is maintained by the operation control unit F obtaining a target flow rate for maintaining the minimum pressure (local minimum value) of the off gas tank pressure at a target pressure (e.g., 2 kPaG) based on pressure detection information from the pressure sensor 14 that detects the off gas tank pressure, and giving the off gas adjustment unit MR an instruction indicating the obtained target flow rate.

Figure 9:
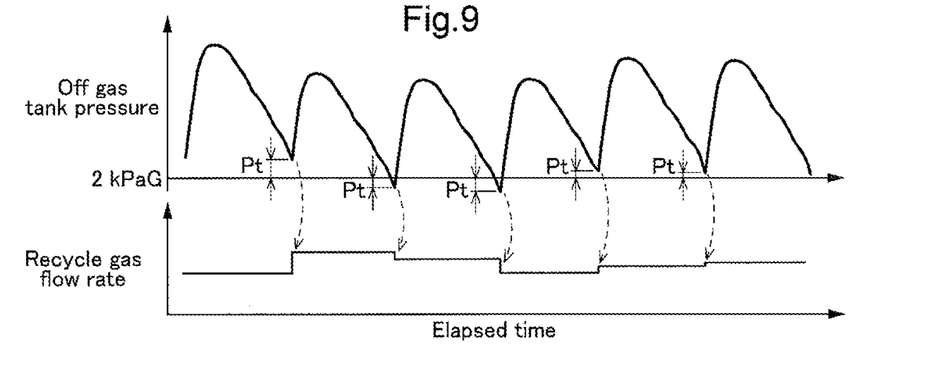
FIG. 9 is a diagram showing a relationship between the off gas tank pressure and a recycle gas flow rate.

Specifically, as shown in FIG. 9, each time the off gas tank pressure of the off gas tank T reaches the minimum pressure (local minimum value), the operation control unit F obtains a pressure difference Pt between that minimum pressure (local minimum value) and the target pressure (e.g., 2 kPaG). A correction flow rate for the target flow rate that is to be given as an instruction to the off gas adjustment unit MR is then obtained based on the obtained pressure difference Pt, the currently instructed target flow rate is corrected using the correction flow rate to obtain a new target flow rate, and the new target flow rate is given as an instruction to the off gas adjustment unit MR.

Figure 10:
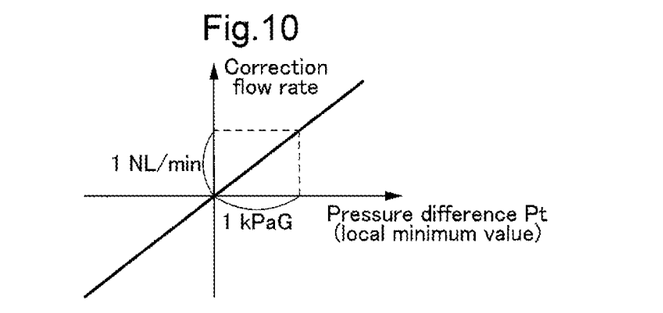
FIG. 10 is a diagram showing a relationship between a pressure difference and a correction flow rate.

As shown in FIG. 10, letting a value of 1 NL/min be obtained as the correction flow rate when the pressure difference Pt is 1 kPaG for example, a larger value is obtained as the correction flow rate the larger the pressure difference Pt is.

As a result, by correcting the recycle gas target flow rate as shown in FIG. 9, the minimum pressure (local minimum value) of the off gas tank pressure approaches the target pressure (e.g., 2 kPaG).

Note that although FIG. 10 illustrates an example in which the relationship between the pressure difference Pt and the correction flow rate is set as a linear expression, the relationship between the pressure difference Pt and the correction flow rate can be modified in various ways, such as setting the relationship between the pressure difference Pt and the correction flow rate as a quadratic expression.

It should be noted that in the present embodiment, as described above, when operation of the pressure swing adsorption type of gas production device is started, the operator uses the operation instruction unit 16 to give the operation control unit F an instruction indicating a target flow rate for recycle gas flowing in the recycle gas return route 11. Specifically, an instruction indicating a target flow rate for maintaining the minimum pressure (local minimum value) of the off gas tank pressure at the target pressure (e.g., 2 kPaG) is given while monitoring the off gas tank pressure detected by the pressure sensor 14.

If an automatic operation instruction is given by the operation instruction unit 16 when the minimum pressure (local minimum value) of the off gas tank pressure reaches the target pressure (e.g., 2 kPaG), the operation control unit F obtains a correction flow rate based on the pressure difference Pt, sets a target flow rate, and gives the off gas adjustment unit MR an instruction indicating the set target flow rate as described above.

Note that a configuration is possible in which even when operation of the pressure swing adsorption type of gas production device starts, the operation control unit F obtains a correction flow rate based on the pressure difference Pt, sets a target flow rate, and gives the off gas adjustment unit MR an instruction indicating the set target flow rate as described above.

Control for Correction of Recycle Gas Flow Rate

In a case of changing/adjusting the adsorption time for which the adsorption process is performed as described above, the operation control unit F changes the target flow rate given to the off gas adjustment unit MR as an instruction in accordance with the change/adjustment, and changes the recycle gas flow rate in a feed-forward manner.

Specifically, in a case of changing the adsorption time, the operation control unit F adjusts the off gas adjustment unit MR such that the recycle gas flow rate is corrected to a flow rate according to which the amount of off gas discharged from an adsorption tower 1 before the change in the adsorption time is equivalent to the amount of off gas discharged from the off gas tank T in the period from when that adsorption tower 1 starts the desorption process after the change in the adsorption time until when another adsorption tower 1 starts the desorption process.

Specifically, when the adsorption time is changed/adjusted, an immediate change occurs in the time for which part of the off gas discharged from one of the four adsorption towers 1 can be returned to the source gas supply route 3 as recycle gas.

Accordingly, immediately after the adsorption time is changed/adjusted, off gas is discharged from the adsorption tower 1 that performed the adsorption process before the adsorption time was changed/adjusted, and therefore the amount of off gas discharged from the adsorption tower 1 does not change immediately after the adsorption time is changed/adjusted.

As a result, when the adsorption time for performing the adsorption process is changed/adjusted to a shorter time, the recycle gas flow rate becomes insufficient, and when the adsorption time for performing the adsorption process is changed/adjusted to a longer time, the recycle gas flow rate becomes excessive, and thus the off gas tank pressure of the off gas tank T becomes excessively high or low.

Figure 11:
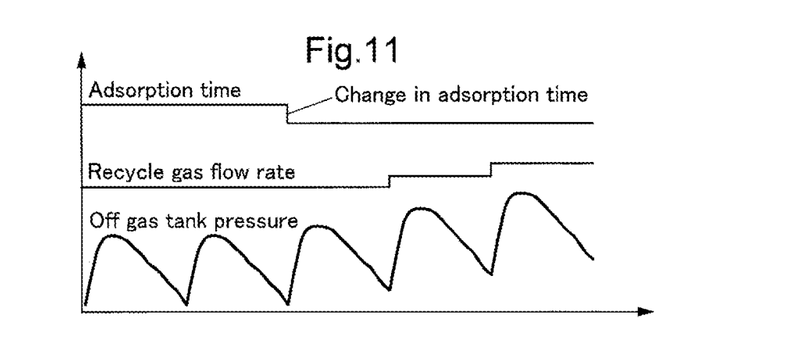
FIG. 11 is a diagram showing a relationship between an adsorption time, the recycle gas flow rate, and the off gas tank pressure.

For example, as shown in FIG. 11, if the adsorption time is changed to a shorter time, the recycle gas flow rate becomes insufficient, and therefore the off gas tank pressure gradually increases.

In the configuration of the present embodiment, if the adsorption time is changed/adjusted, the recycle gas flow rate is maintained at an appropriate flow rate by changing the recycle gas flow rate in a feed-forward manner in accordance with the change/adjustment.

Specifically, in the case where the adsorption time is changed/adjusted such that the product of a reference time and the recycle gas flow rate is constant, the operation control unit F changes the target flow rate that is given to the off gas adjustment unit MR as an instruction in accordance with the change/adjustment.

The reference time is a time that corresponds to the period of discharge of off gas from each of the adsorption towers 1, that is to say the time from when the discharge of off gas from one adsorption tower 1 starts until when the discharge of off gas from the next adsorption tower 1 starts.

Specific examples include the time corresponding to steps 4 to 7 from when the discharge of off gas from the tower D starts until when the discharge of off gas from the tower A starts, the time corresponding to steps 8 to 11 from when the discharge of off gas from the tower A starts until when the discharge of off gas from the tower B starts, the time corresponding to steps 12 to 15 from when the discharge of off gas from the tower B starts until when the discharge of off gas from the tower C starts, and the time corresponding to steps 16 to 3 in the tower A from when the discharge of off gas from the tower C starts until when the discharge of off gas from the tower D starts, and these times each include the adsorption time correction value X.

Accordingly, in the case where the adsorption time is changed/adjusted, the product of the reference time at the time before the change/adjustment of the adsorption time and the recycle gas flow rate is divided by the reference time at the time after the change/adjustment of the adsorption time, thus obtaining a recycle gas flow rate that is the new target, and the obtained recycle gas flow rate is set as the target flow rate and given to the off gas adjustment unit MR as an instruction.

Figure 12:
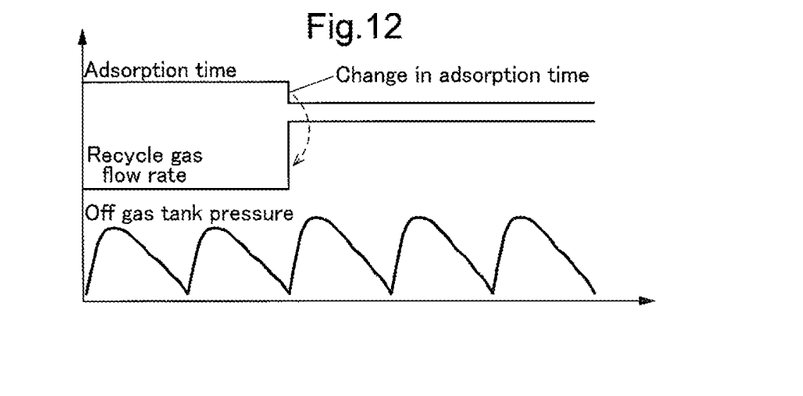
FIG. 12 is a diagram showing a relationship between the adsorption time, the recycle gas flow rate, and the off gas tank pressure.

For example, as shown in FIG. 12, if the adsorption time is changed to a shorter time, the recycle gas flow rate is increased, thus suppressing an increase in the off gas tank pressure.

Also, although not shown in the drawings, if the adsorption time is changed to a longer time, the recycle gas flow rate is reduced, thus suppressing a decrease in the off gas tank pressure.

Control for Correcting Supply of Source Gas

The operation control unit F is configured to, in the case of increasing or reducing the recycle gas flow rate through the "control for correcting recycle gas flow rate" described above, correct the amount of source gas G supplied to the adsorption towers 1 by giving the source gas adjustment unit MG an instruction indicating a target amount for the source gas supply amount, which is reduced or increased by an amount corresponding to the increase or decrease in the recycle gas flow rate.

In other words, if the recycle gas flow rate is increased, the amount of gas supplied to an adsorption tower 1 increases rapidly, and therefore the amount of miscellaneous gas supplied to the adsorption tower 1 increases, and there is a risk of a decrease in the concentration of methane in the product gas H.

In the present embodiment, when the adsorption time is changed to a shorter time through the "control for adjusting adsorption time", if the recycle gas flow rate is accordingly increased through the "control for correcting recycle gas flow rate", the source gas G supply amount is reduced by an amount that corresponds to the increase in the recycle gas flow rate, thus making it possible to suppress a decrease in the concentration of methane in the product gas H.

Second Embodiment

Next, a second embodiment of the pressure swing adsorption type of gas production device is described. This second embodiment shows another aspect of the "control for adjusting the adsorption time" in the first embodiment, and because the basic configuration is similar to that in the first embodiment, the following describes only details of aspects that are different from the first embodiment.

The first embodiment shows an example in which the operation control unit F changes/adjusts the adsorption time for which the adsorption process is performed based on detection information from the source-side concentration sensor SG, whereas in the second embodiment, the adsorption time is changed/adjusted based on detection information from the product-side concentration sensor SH.

Figure 13:
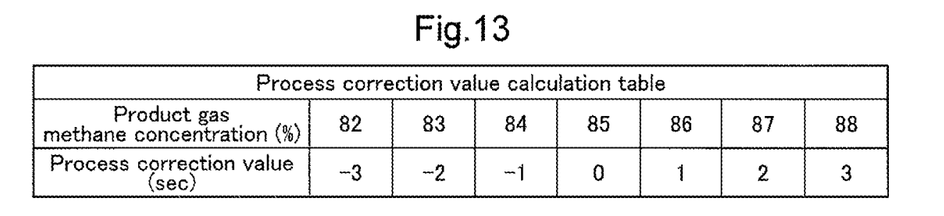
FIG. 13 is a table showing a relationship between a methane concentration in a product gas and a process correction value in a second embodiment.

Specifically, as shown in the table in FIG. 13, a relationship is determined in advance for the process correction value and the concentration of methane gas in the product gas detected by the product-side concentration sensor SH.

When the pressure swing adsorption type of gas production device starts to operate, operation starts with a pre-set initial value (e.g., 100 seconds) as the adsorption time correction value X, and thereafter, each time the adsorption process is performed by the adsorption towers 1, the average value of the concentration of methane in the product gas in the corresponding cycle is obtained as the average source gas methane concentration. Note that the average product gas methane concentration is obtained by sampling the detection information from the product-side concentration sensor SH at a set time interval (e.g., 500 ms) and obtaining the average value of the sampled detection values.

Figure 14:
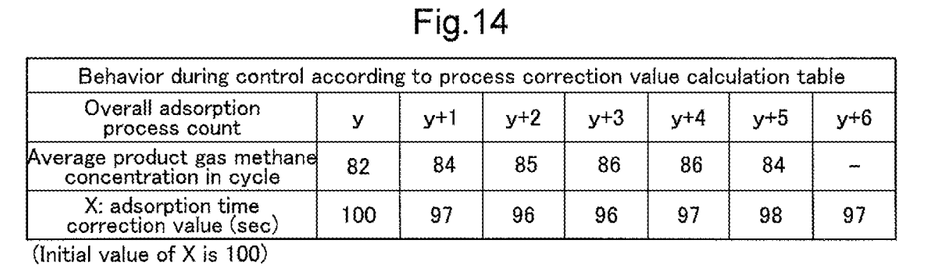
FIG. 14 is a table showing the behavior of an adsorption time correction value in the second embodiment.

Next, as shown in FIG. 14, when the adsorption process in the first cycle ends, a process correction value is obtained based on the average product gas methane concentration and the relationship in FIG. 13, and the obtained process correction value is added to the current adsorption time correction value (initial value) X to obtain a new adsorption time correction value X for the next adsorption process.

Thereafter, when the adsorption process in the second and subsequent cycle ends, a process correction value is obtained based on the average product gas methane concentration and the relationship in FIG. 13, the obtained process correction value is added to all of the process correction values obtained at the end of the adsorption process in previous cycles to obtain an integrated value, and the integrated value is added to the initial value (e.g., 100 seconds) to obtain a new adsorption time correction value X for the next adsorption process.

For example, when the adsorption process corresponding to first overall adsorption process count y is executed with the adsorption time correction value X of 100 [sec], if the average product gas methane concentration is 82[%], then in the next adsorption process corresponding to the overall adsorption process count y+1, the initial value of "100 [sec]" and the process correction value "−3 [sec]" are added to obtain the adsorption time correction value X of "97 [sec]".

Next, when the second adsorption process ends, if the average product gas methane concentration in the current cycle is 84[%], then in the next adsorption process corresponding to the overall adsorption process count y+2, the initial value of "100 [sec]", the process correction value "−3 [sec]" of the first cycle, and the process correction value "−1 [sec]" of the second cycle are added to obtain the adsorption time correction value X of "96 [sec]".

The same follows for the subsequent adsorption processes corresponding to overall adsorption process counts y+3 to y+6.

In the second embodiment as well, a rapid change in the off gas tank pressure is suppressed by performing the "control for correcting recycle gas flow rate".

In particular, in the case where the adsorption time is corrected based on the concentration of methane gas in the product gas, if the adsorption time for performing the adsorption process is changed/adjusted to a shorter time, the recycle gas flow rate becomes insufficient, and the off gas tank pressure increases, thus leading to a degradation in the adsorption conditions in the desorption process (pressure reduction) in the adsorption towers 1, and desorption of the miscellaneous gas cannot be performed appropriately. There is a risk that this leads to an abnormal situation in which control cannot be performed, such as a situation in which the adsorption time is repeatedly changed/adjusted to a shorter time, such that the adsorption time becomes excessively short, and the recycle gas flow rate rises excessively. However, the occurrence of such an abnormal situation can be suppressed by performing the "control for correcting recycle gas flow rate".

In the second embodiment as well, a decrease in the concentration of methane gas in the product gas can be suppressed by performing the "control for correcting source gas supply".

In particular, in the case where the adsorption time is corrected based on the concentration of methane gas in the product gas, if the recycle gas flow rate is increased, the amount of miscellaneous gas supplied to the adsorption towers 1 increases, and the concentration of methane in the product gas H decreases, then there is a risk of leading to an abnormal situation in which a decrease in the concentration of methane in the product gas H continues due to repeatedly correcting the adsorption time to a shorter time and increasing the recycle flow rate. However, the occurrence of such an abnormal situation can be suppressed by performing the "control for correcting source gas supply".

Third Embodiment

Next, a third embodiment of the pressure swing adsorption type of gas production device is described. This third embodiment shows another aspect of the "control for adjusting the adsorption time" in the first embodiment, and because the basic configuration is similar to that in the first embodiment, the following describes only details of aspects that are different from the first embodiment.

In the third embodiment, the operation control unit F controls/adjusts the adsorption time for which the adsorption process is performed based on detection information from the source-side concentration sensor SG and detection information from the product-side concentration sensor SH.

Figure 15:
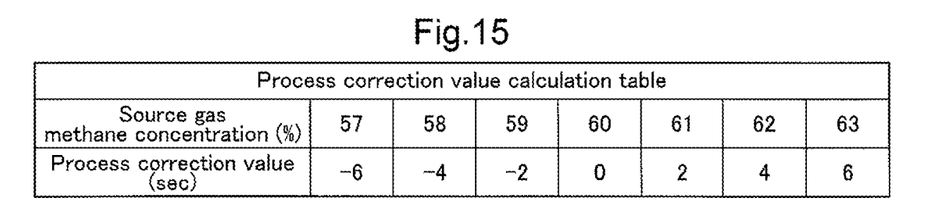
FIG. 15 is a table showing a relationship between a methane concentration in a source gas and a process correction value in a third embodiment.
Figure 16:
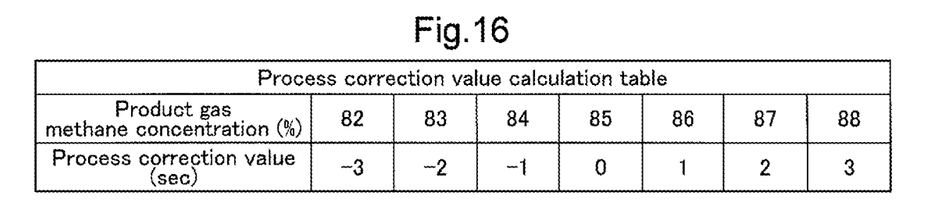
FIG. 16 is a table showing a relationship between a methane concentration in a product gas and a process correction value in the third embodiment.

Specifically, as shown in the table in FIG. 15, a relationship is determined in advance for the process correction value and the concentration of methane gas in the source gas detected by the source-side concentration sensor SG, and as shown in the table in FIG. 16, a relationship is determined in advance for the process correction value and the concentration of methane gas in the product gas detected by the product-side concentration sensor SH.

When the pressure swing adsorption type of gas production device starts to operate, operation starts with a pre-set initial value (e.g., 100 seconds) as the adsorption time correction value X.

Thereafter, each time the adsorption process is performed by the adsorption towers 1, the average value of the concentration of methane in the source gas in the corresponding cycle is obtained as the average source gas methane concentration, and the average value of the product gas methane concentration in the corresponding cycle is obtained as the average product gas methane concentration.

Note that the average source gas methane concentration is obtained by sampling the detection information from the source-side concentration sensor SG at a set time interval (e.g., 500 ms) and obtaining the average value of the sampled detection values, and similarly, the average product gas methane concentration is obtained by sampling the detection information from the product-side concentration sensor SH at a set time interval (e.g., 500 ms) and obtaining the average value of the sampled detection values.

Next, the process correction value for the source gas G is obtained based on the average source gas methane concentration and the relationship in FIG. 15, and similarly, the process correction value for the product gas H is obtained based on the average product gas methane concentration and the relationship in FIG. 16.

Figure 17:
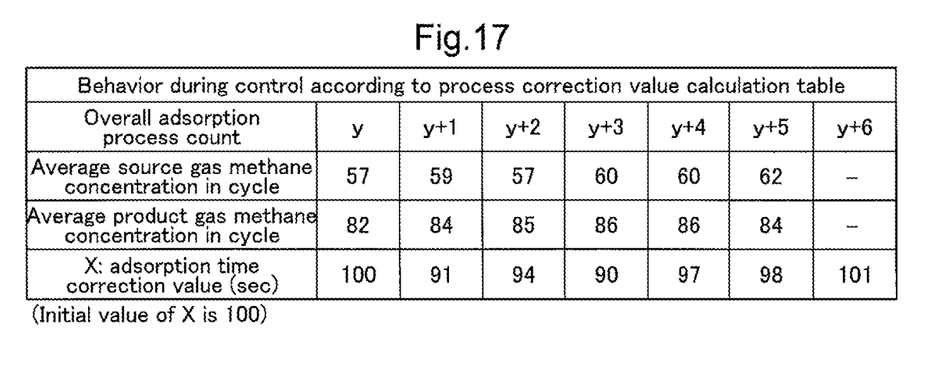
FIG. 17 is a table showing the behavior of an adsorption time correction value in the third embodiment.

As shown in FIG. 17, the current adsorption time correction value (initial value) X and the process correction value for the source gas G corresponding to the adsorption process in the immediately previous cycle are added to the value which has been obtained by summing the process correction value for the product gas H corresponding to the adsorption process in the immediately previous cycle and the integrated value of the process correction values for the product gas H obtained at the end of the adsorption process in the previous cycles, and the resulting value is set as the adsorption time correction value X for the next adsorption process.

For example, when the adsorption process corresponding to first overall adsorption process count y is executed with the adsorption time correction value X of 100 [sec], if the source gas methane concentration is 57[%] and the average product gas methane concentration is 82[%], then in the next adsorption process corresponding to the overall adsorption process count y+1, the initial value of "100 [sec]", the process correction value of "−6 [sec]" for the source gas G, and the process correction value of "−3 [sec]" for the product gas H are added to obtain the adsorption time correction value X of "91 [sec]".

Next, when the second adsorption process ends, if the average source gas methane concentration is 59[%] and the average product gas methane concentration is 84[%], the process correction value "−2 [sec]" for the source gas G and the process correction value "−1 [sec]" for the product gas H are obtained, and the process correction value "−3 [sec]" for the product gas H in the immediately previous adsorption process corresponding to the overall adsorption process count y and the process correction value "−1 [sec]" for the product gas H in the current adsorption process corresponding to the overall adsorption process count y+1 are added to obtain the integrated value of "−4 [sec]" as the process correction value for the product gas H.

Then the initial value of "100 [sec]", the process correction value of "−2 [sec]" for the source gas G, and the integrated value of "−4 [sec]" of the process correction values for the product gas H are added to obtain "94 [sec]" as the adsorption time correction value X.

The same follows for the subsequent cycles y+3 to y+6.

In the third embodiment as well, a rapid change in the off gas tank pressure is suppressed by performing the "control for correcting recycle gas flow rate".

In particular, in the case where the adsorption time is corrected based on the product gas methane gas concentration, if the adsorption time for performing the adsorption process is changed/adjusted to a shorter time, the recycle gas flow rate becomes insufficient, and the off gas tank pressure increases, thus leading to a degradation in the adsorption conditions in the desorption process (pressure reduction) in the adsorption towers 1, and desorption of the miscellaneous gas cannot be performed appropriately. There is a risk that this leads to an abnormal situation in which control cannot be performed, such as a situation in which the adsorption time is repeatedly changed/adjusted to a shorter time, such that the adsorption time becomes excessively short, and the recycle gas flow rate rises excessively. However, the occurrence of such an abnormal situation can be suppressed by performing the "control for correcting recycle gas flow rate".

In the third embodiment as well, a decrease in the concentration of methane gas in the product gas can be suppressed by performing the "control for correcting source gas supply".

In particular, in the case where the adsorption time is corrected based on the concentration of methane gas in the product gas, if the recycle gas flow rate is increased, the amount of miscellaneous gas supplied to the adsorption towers 1 increases, and the concentration of methane in the product gas H decreases, there is a risk of leading to an abnormal situation in which a decrease in the concentration of methane in the product gas H continues due to repeatedly correcting the adsorption time to a shorter time and increasing the recycle flow rate. However, the occurrence of such an abnormal situation can be suppressed by performing the "control for correcting source gas supply".

Other Embodiments

The following describes other embodiments.

(1) In the first to third embodiments, the off gas adjustment unit MR, which adjusts the discharge flow rate of off gas discharged from the off gas tank T, is provided at a location downstream of the membrane separation unit 9, but an aspect is possible in which the off gas adjustment unit MR is provided at a location that is between the booster pump 10 and the membrane separation unit 9.

(2) The first to third embodiments illustrate a case where the source supply amount is corrected so as to be reduced in accordance with the amount of increase in the recycle gas in the "control for correcting supply of source gas", but a configuration is possible in which the concentration of miscellaneous gas in the recycle gas is detected, and the source supply amount is corrected so as to be reduced by an amount corresponding to the amount of increase in the amount of miscellaneous gas in the recycle gas.

(3) The first to third embodiments illustrate the case where the off gas adjustment unit MR is configured using a massflow controller, but the off gas adjustment unit MR may be configured so as to adjust the discharge amount of the booster pump 10 that constitutes the pressure boosting unit while detecting the gas flow rate with use of a flow rate sensor.

(4) The first to third embodiments describe cases where the source gas G is a biogas that contains methane as the purification target gas and contains carbon dioxide or the like as the miscellaneous gas, but the source gas G may be, for example, a gas obtained by reforming city gas, that is to say the source gas G can be any of various types of gas, such as a gas that contains hydrogen as the purification target gas and contains carbon dioxide, carbon monoxide, and nitrogen as miscellaneous gases.

(5) The first to third embodiments describe an apparatus that includes four adsorption towers 1 as the pressure swing adsorption type of gas production device, but a configuration is possible in which the apparatus includes three or five or more adsorption towers 1, and the adsorption towers 1 successively execute, with different phases, the adsorption process, the pressure-reducing pressure equalization process, the desorption process, and the pressure-boosting pressure equalization process.

(6) The first to third embodiments describe aspects in which the source gas supply route 3 and the off gas discharge route 4 are connected to the lower end side of each of the adsorption towers 1 as the one end side, and the purification target gas discharge route 5 is connected to the upper end side of each the adsorption towers 1 as the other end side, but an aspect is possible in which the source gas supply route 3 and the off gas discharge route 4 are connected to the upper end side of each of the adsorption towers 1 as the one end side, and the purification target gas discharge route 5 is connected to the lower end side of each the adsorption towers 1 as the other end side.

Also, the off gas discharge route 4 may be connected to the adsorption towers 1 on the side of the adsorption towers 1 corresponding to the end portions that are connected to the purification target gas discharge route 5, or may be connected at an intermediate portion in the lengthwise direction of the adsorption towers 1, or in other words, it is sufficient that the off gas discharge route 5 is connected to the adsorption towers 1.

Note that the configurations disclosed in each of the embodiments described above (including the alternative embodiments; the same applies to the following) can be applied in combination with configurations disclosed in other embodiments as long as no contradiction arises. Also, the embodiments disclosed in this specification are illustrative, embodiments of the present invention are not limited to the disclosed embodiments, and appropriate modifications can be made without departing from the object of the present invention.

DESCRIPTION OF REFERENCE SIGNS

1 adsorption tower
3 source gas supply route
4 off gas discharge route
5 purification target gas discharge route (product gas feed route)
9 A separation membrane
11 membrane separation unit
11 recycle gas return route
12 off gas adjustment unit
14 pressure sensor
15 source gas adjustment unit
F operation control unit
G source gas (biogas)
H purification target gas (product gas)
T off gas tank

The invention claimed is:

1. A pressure swing adsorption type of gas production device comprising:
   a plurality of adsorption towers that are each filled with an adsorbent to which a miscellaneous gas is adsorbed from a source gas that includes a purification target gas and the miscellaneous gas, a source gas supply route being connected to one end side of each of the adsorption towers, a purification target gas discharge route being connected to another end side of each of the adsorption towers, and an off gas discharge route being connected to each of the adsorption towers;
   an operation control unit that causes the adsorption towers to successively perform, with different phases, an operation cycle that includes an adsorption process in which the miscellaneous gas is adsorbed from the source gas supplied via the source gas supply route such that the purification target gas is discharged via the purification target gas discharge route, and a desorption process in which the miscellaneous gas is discharged via the off gas discharge route;
   a membrane separation unit that is provided in the off gas discharge route and includes a separation membrane that allows the miscellaneous gas to pass faster than the purification target gas; and
   a recycle gas return route via which recycle gas that did not pass through the separation membrane is returned to the source gas supply route,
   wherein a pressure boosting unit and an off gas tank are provided on an upstream side of the membrane separation unit in the off gas discharge route, the off gas tank storing off gas that is discharged via the off gas discharge route in the desorption process, and the pressure boosting unit raising a pressure of the off gas stored in the off gas tank and supplying the off gas to the membrane separation unit for membrane separation in the membrane separation unit,
   the pressure swing adsorption type of gas production device further comprises an off gas adjustment unit that adjusts a discharge flow rate of the off gas that is discharged from the off gas tank, and
   the operation control unit adjusts the off gas adjustment unit such that the discharge flow rate of the off gas is a flow rate according to which the amount of off gas discharged from one of the adsorption towers each time the desorption process is performed is equivalent to the amount of off gas discharged from the off gas tank in a period from when the one adsorption tower starts the desorption process until when another adsorption tower starts the desorption process.

2. The pressure swing adsorption type of gas production device according to claim 1, further comprising
   a pressure sensor that detects an internal pressure in the off gas tank,
   wherein the operation control unit adjusts, based on detection information from the pressure sensor, the off gas adjustment unit such that the discharge flow rate of the off gas is a flow rate according to which a local minimum value of the internal pressure of the off gas tank, which repeatedly increases and decreases, is maintained at a set pressure.

3. The pressure swing adsorption type of gas production device according to claim 2,
   wherein the operation control unit changes an adsorption time for which the adsorption process is performed, based on at least one of a concentration of the purification target gas in the source gas and a concentration of the purification target gas discharged from the adsorption tower, and in a case of changing the adsorption time, the operation control unit adjusts the off gas adjustment unit so as to correct the discharge flow rate of the off gas discharged from the off gas tank to a flow rate according to which the amount of off gas discharged from one of the adsorption towers before the change in the adsorption time is equivalent to the amount of off gas discharged from the off gas tank in a period from when the one adsorption tower starts the desorption process after the change in the adsorption time until when another adsorption tower starts the desorption process.

4. The pressure swing adsorption type of gas production device according to claim 3, further comprising
a source gas adjustment unit that adjusts a source gas supply rate of source gas supplied to the adsorption tower via the source gas supply route,
wherein the operation control unit adjusts the source gas adjustment unit so as to correct the source gas supply rate to a lower value in a case where the discharge flow rate of the off gas tank is corrected to a higher value, and to correct the source gas supply rate to a higher value in a case where the discharge flow rate is corrected to a lower value.

5. The pressure swing adsorption type of gas production device according to claim 1,
wherein the source gas is a methane-containing gas that contains 40% or more methane as the purification target gas, and the purification target gas discharged via the purification target gas discharge route is a product gas that contains 80% or more methane.

6. The pressure swing adsorption type of gas production device according to claim 2,
wherein the source gas is a methane-containing gas that contains 40% or more methane as the purification target gas, and the purification target gas discharged via the purification target gas discharge route is a product gas that contains 80% or more methane.

7. The pressure swing adsorption type of gas production device according to claim 3,
wherein the source gas is a methane-containing gas that contains 40% or more methane as the purification target gas, and the purification target gas discharged via the purification target gas discharge route is a product gas that contains 80% or more methane.

8. The pressure swing adsorption type of gas production device according to claim 4,
wherein the source gas is a methane-containing gas that contains 40% or more methane as the purification target gas, and the purification target gas discharged via the purification target gas discharge route is a product gas that contains 80% or more methane.

* * * * *

UNITED STATES PATENT AND TRADEMARK OFFICE
CERTIFICATE OF CORRECTION

PATENT NO. : 10,710,019 B2
APPLICATION NO. : 16/088571
DATED : July 14, 2020
INVENTOR(S) : Hiroshi Tanaka et al.

Page 1 of 1

It is certified that error appears in the above-identified patent and that said Letters Patent is hereby corrected as shown below:

In the Specification

Column 1, Line 3, above "This" insert -- CROSS-REFERENCE TO RELATED APPLICATIONS --

Signed and Sealed this
Tenth Day of November, 2020

Andrei Iancu
*Director of the United States Patent and Trademark Office*